US006867001B2

(12) United States Patent
Kondo et al.

(10) Patent No.: US 6,867,001 B2
(45) Date of Patent: Mar. 15, 2005

(54) METHOD FOR PROCESSING A LIBRARY USING LIGATION INHIBITION

(75) Inventors: Kazuhiro Kondo, Chiba (JP); Michio Oishi, Chiba (JP); Osamu Ohara, Chiba (JP)

(73) Assignees: Aisin Cosmos R&D Co., Ltd., Kisarazu (JP); Kazusa DNA Research Institute Foundation, Kisarazu (JP)

( * ) Notice: Subject to any disclaimer, the term of this patent is extended or adjusted under 35 U.S.C. 154(b) by 230 days.

(21) Appl. No.: 10/253,319

(22) Filed: Sep. 24, 2002

(65) Prior Publication Data

US 2003/0064404 A1 Apr. 3, 2003

(30) Foreign Application Priority Data

Sep. 25, 2001 (JP) ........................................ 2001-291800
Sep. 11, 2002 (JP) ........................................ 2002-265911

(51) Int. Cl.[7] .......................... C12Q 1/68; C07H 21/04; C12P 19/34
(52) U.S. Cl. .......................... 435/6; 435/91.1; 536/23.1
(58) Field of Search ............................... 435/6, 91.1, 5; 536/23.1

(56) References Cited

U.S. PATENT DOCUMENTS

| 4,888,274 A | * | 12/1989 | Radding et al. ............... 435/6 |
| 5,482,845 A | | 1/1996 | Soares et al. |
| 5,565,340 A | | 10/1996 | Chenchik et al. |
| 2002/0058268 A1 | | 5/2002 | Kondo et al. |

FOREIGN PATENT DOCUMENTS

| EP | 1 065 279 A1 | 1/2001 |
| JP | 2002-209590 A | 7/2002 |
| WO | WO 96/18732 A2 | 6/1996 |
| WO | WO 98/50541 A1 | 11/1998 |

OTHER PUBLICATIONS

Bonaldo, M.F., et al., "Normalization and Subtraction: Two Approaches to Facilitate Gene Discovery," *Genome Research* 6(9):791–806, 1996.

Diatchenko, L., et al., "Suppression Subtractive Hybridization: A Versatile Method for Identifying Differentially Expressed Genes," *Methods Enzymol.* 303:349–380, 1999.

Hedrick, S.M., et al., "Isolation of cDNA Clones Encoding T Cell–Specific Membrane–Associated Proteins," *Nature* 308(5955):149–153, 1984.

Zhumabayeva, B., et al., "RecA–Mediated Affinity Capture: A Method for Full–Length cDNA Cloning," *BioTechniques* 27:834–845, Oct. 1999.

Frank–Kamenetskii, M.D., and S.M. Mirkin, "Triplex DNA Structures," *Annual Review of Biochemistry* 64:65–95, 1995.

Rigas, B., et al., "Rapid Plasmid Library Screening Using RecA–Coated Biotinylated Probes," *Proceedings of the National Academy of Sciences of the United States* 83:9591–9595, Dec. 1986.

Kowalczykowski, S.C., and A.K. Eggleston, "Homologous Pairing and DNA Strand–Exchange Proteins," *Annu. Rev. Biochem.* 63:991–1043, 1994.

(List continued on next page.)

*Primary Examiner*—Jehanne Sitton
*Assistant Examiner*—Sarae Bausch
(74) *Attorney, Agent, or Firm*—Christensen O'Connor Johnson Kindness PLLC (57) ABSTRACT

An objective of this invention is to provide a method which can specifically enrich a desired DNA with a long insert size from a DNA library and can provide a clone of the DNA directly. This invention provides a method of constructing a DNA library having increased proportion of a first double-stranded DNA therein by removing, from an original library containing the first double-stranded DNA to be increased in proportion, a second double-stranded DNA different from the first double-stranded DNA.

4 Claims, 3 Drawing Sheets

OTHER PUBLICATIONS

Rao, B.J. et al., "Stable Three–Stranded DNA Made by RecA Protein," *Proc. Natl. Acad. Sci. USA* 88(8):2984–2988, 1991.

Rigas, B., et al., "Rapid Plasma Library Screening Using RecA–Coated Biotinylated Probes," *Proc. Natl. Acad. Sci. USA* 83(24):9591–9595, 1986.

Rubenstein, J.L.R., et al., "Subtractive Hybridization System Using Single–Stranded Phagemids With Directional Inserts," *Nucleic Acids Research* 18(16):4833, 1990.

Zhumabayeva, B., et al., "General of Full–Length cDNA Libraries Enriched for Differentially Expressed Genes for Functional Genomics," *BioTechniques* 30:(3):512–520, 2001.

* cited by examiner

METHOD FOR PROCESSING A LIBRARY USING LIGATION INHIBITION

CROSS-REFERENCE TO RELATED APPLICATIONS

This application is based upon and claims the benefit of priority from the prior Japanese Patent Applications No. 2001-291800, filed Sep. 25, 2001; and No. 2002-265911, filed Sep. 11, 2002, the entire contents of both of which are incorporated herein by reference.

BACKGROUND OF THE INVENTION

1. Field of the Invention

The present invention relates to a method for constructing a DNA library having increased proportion of a desired nucleic acid by removing, from an original DNA library, a nucleic acid other than the desired nucleic acid using RecA protein.

2. Description of the Related Art

DNA libraries, particularly cDNA libraries, are very useful tools for gene cloning. To date, various genes have been cloned from cDNA libraries. A cloned gene is used to determine an amino acid sequence of a protein encoded by the gene and to produce a large amount of the protein in bacterial or yeast cells, as well as to determine its nucleotide sequence.

However, cDNAs that can be easily cloned from a cDNA library are restricted to those whose template mRNAs are abundantly expressed in a cell. It is getting harder to clone a novel cDNA with high efficiency, because cDNAs easy for cloning have now mostly been cloned.

In order to efficiently clone novel cDNAs from a cDNA library, it is necessary to remove cDNAs already cloned from the library. For this purpose, the following prior arts have been devised.

Subtractive hybridization has been used primarily for this purpose. In this method, mRNAs are harvested both from cells (or tissues) expressing genes of interest and those not expressing them. Then cDNAs are synthesized from the mRNAs in either cell. Through hybridization of the synthesized cDNAs with the mRNAs, cDNAs that are present in both cells are selectively removed. This enables enrichment and isolation of genes specifically expressed in a particular tissue or a cell.

"Genome Res. 1996 Sep: 6(9): pp. 791–806" discloses subtractive hybridization using a hydroxyapatite column. In this method, primers from vector-derived sequences are elongated using a single-stranded DNA library as templates. After denaturation and annealing, DNAs that form a double strand again are specifically removed by the column. Since probability of annealing is dependent on concentration, abundant clones are preferentially removed.

However, this method can only be applied to relatively short cDNAs approximately 0.4–2.5 kb in size, because non-specific hybridization can occur when cDNA libraries are used that include long sequences with an insert size greater than 3 kb. Long sequences are often found to be a functionally important gene encoding a multifunctional protein or a protein with complex conformation. Therefore, it is a major drawback of this method that it cannot be applied to a library containing a long sequence. Furthermore, this method cannot distinguish even short cDNAs, if their sequences are derived from an identical gene and have common sequences at 3' and 5' ends only, not in their central regions.

Other method widely used for a similar purpose is differential hybridization.

In this method, cDNA probes are synthesized with mRNAs prepared both from control cells and cells of interest from which a specific gene is obtained. A cDNA library generated from the cells of interest is then plated, and colonies on the same plate are replica-plated onto two filters. For one filter, hybridization is performed with cDNA probes from the cells of interest. For the other, hybridization is performed with cDNA probes from the control cells. cDNAs specific for the cells of interest can be detected by comparing the results.

However, in this method, differences in hybridization between two filters must be compared from colony to colony. Accordingly, it is difficult to handle numerous colonies by the method. This method is thus not suitable for reconstitution of a whole library. This method has an additional drawback of being time-consuming for checking many possible pseudo-positive or pseudo-negative signals.

To overcome such drawbacks of this method, "Methods in Enzymology 1995: 254: pp. 304–321" discloses differential display method, which is a combination of conventional differential hybridization and polymerase chain reaction (hereinafter referred to as "PCR"). However, this method can detect a difference in a pattern only when the difference in an expression level is significant. In addition, it is necessary to select clones by any method based on a PCR product, because this method cannot produce clones directly.

BRIEF SUMMARY OF THE INVENTION

The present invention is made to solve above problems resided in prior arts. Accordingly, the objective of the invention is to provide a method that is capable of specifically enriching a desired DNA with a long insert size in a DNA library, and directly providing a clone of the DNA.

In a first embodiment of the invention, there is provided a method of constructing a circular DNA library having increased proportion of a first double-stranded DNA to be increased in proportion, by removing, from an original circular DNA library, a second double-stranded DNA that is not identical to the first double-stranded DNA, the method comprises the following steps of;

(1) linearizing circular DNAs in the original circular DNA library to obtain a linear DNA library;

(2) preparing a single-stranded DNA corresponding to the second double-stranded DNA;

(3) adding, to the linear DNA library, RecA protein and the second single-stranded DNA prepared in the step (2) to produce triplexed DNA through the binding of the second single-stranded DNA to the second double-stranded DNA via the RecA protein;

(4) subjecting linear DNA containing the triplexed DNA prepared in the step (3) to ligation to selectively circularize double-stranded DNA not having triplex structure;

(5) removing linear DNA from the DNA subjected to treatment in the step (4) thereby constructing a DNA library having increased proportion of the first double-stranded DNA.

Particularly there is provided the methods wherein the linear DNAs are removed from the DNAs subjected to treatment in the step (4) by transforming a host with the DNAs obtained in the step (4) to select a host transformed with circular DNA using a drug.

In a second embodiment of the present invention, there is provided a method of constructing a DNA library having increased proportion of a first double-stranded DNA to be increased in proportion, by removing, from an original circular DNA library, a second double-stranded DNA that is not identical to the first double-stranded DNA, the method comprises the following steps of;

(1) preparing a linear DNA library containing the first double-stranded DNA;

(2) preparing single-stranded DNAs corresponding to both ends of the second double-stranded DNA;

(3) adding, to the linear DNA, RecA protein and the second single-stranded DNA prepared in the step (2) to produce triplexed DNA through the binding of the second single-stranded DNA to the second double-stranded DNA via the RecA protein;

(4) subjecting the linear DNA containing the triplexed DNA prepared in the step (3) to ligation with a desired DNA to selectively circularize double-stranded DNA not having triplex structure;

(5) removing the linear DNA from the DNA subjected to treatment in the step (4) thereby constructing a DNA library having increased proportion of the first double-stranded DNA.

Particularly there is provided the method wherein the linear DNAs is removed from the DNA subjected to treatment in the step (4) by transforming a host with the DNAs obtained in the step (4) to select a host transformed with circular DNA using a drug.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

This invention was made based on a finding by the inventors that triplex structure is retained even after dissociation of RecA protein from the structure, when the structure is formed via RecA protein in a terminal region of a target nucleic acid. RecA protein and the formation of the triplex structure by RecA protein is known.

Here, a description of RecA protein will be given.

RecA protein is known to be involved in homologous recombination, DNA repair, and expression of SOS gene in *E. Coli*. RecA proteins from *E. Coli* and lambda phage are most popular. However, it is known that proteins having similar structure and function to those of RecA protein of *E. Coli* are widely distributed in organisms other than *E. Coli*, and are generally referred to as RecA-like protein.

Figure 1:
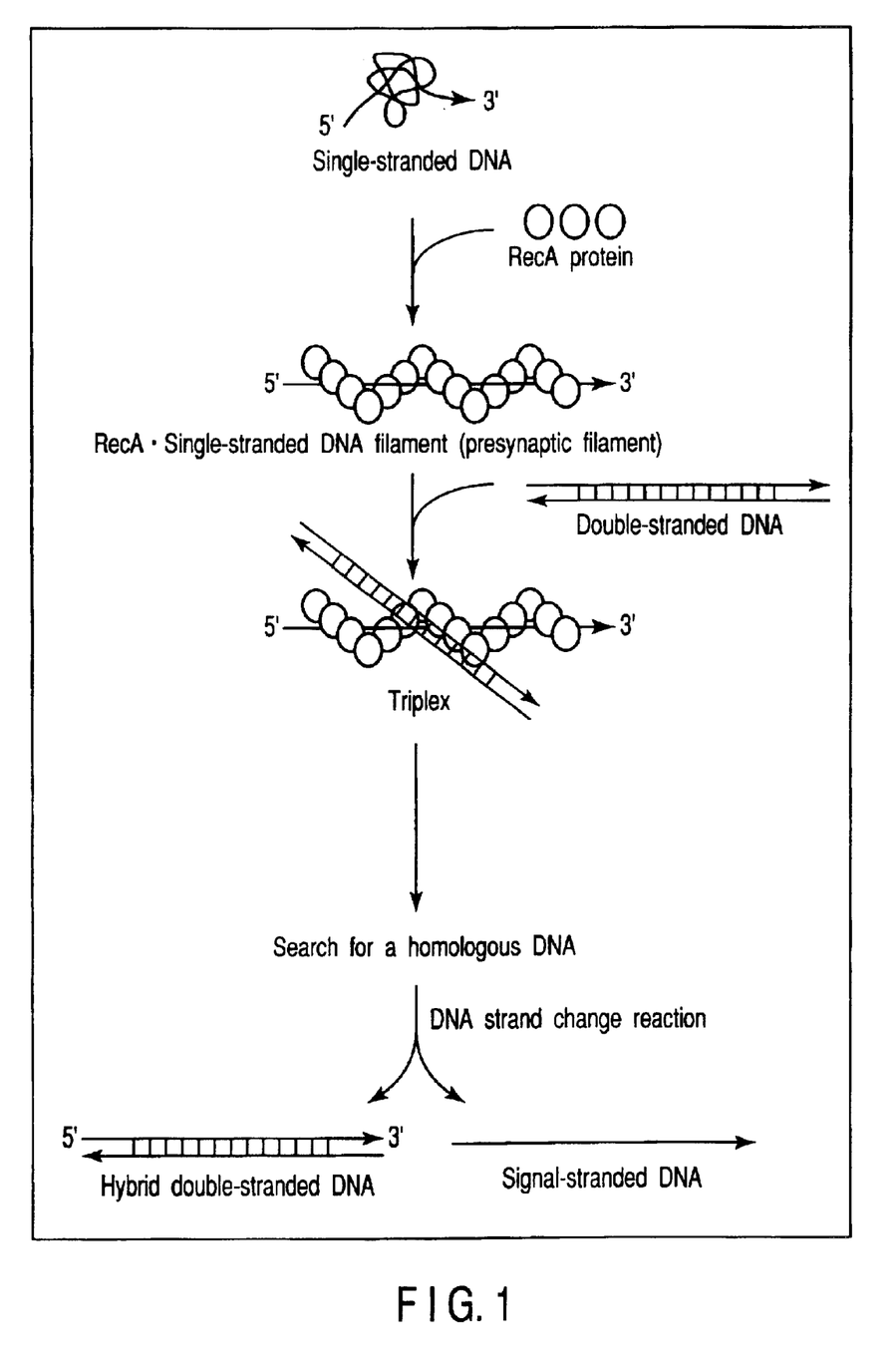
FIG. 1 is a schematic diagram of a mode of action of RecA protein.

As shown in FIG. 1, RecA protein binds to a single-stranded DNA (RecA-ssDNA fiber) and associates the single-stranded DNA with a double-stranded DNA to give rise to a triplex. Then it searches for a homologous DNA, and catalyzes DNA strand exchange reaction in the presence of ATP. After the reaction, a hybrid dsDNA, which consists of the dsDNA into which the ssDNA is incorporated, and an ssDNA excised from the dsDNA are formed.

As described above, RecA protein does not bind a single-stranded nucleic acid randomly to a double-stranded nucleic acid, but to a homologous region located in either strand of a double-stranded DNA. As used herein, the phrase that two nucleic acids are "homologous" means that they are equivalent or similar enough to allow formation of specific triplex structure via RecA protein. As used herein, the term "similar" refers to, for example, at least 50% or more, preferably 80% or more, more preferably 90% or more, and even more preferably 95% or more identity between the two nucleic acids.

The present invention is a method of removing a defined DNA from a DNA library utilizing the formation of triplex structure DNA by the binding of a single-stranded DNA to a homologous double-stranded DNA via RecA protein.

As used herein, the term "RecA protein" means a protein having an ability to bind a single-stranded nucleic acid to any region in one strand of a double-stranded nucleic acid that is homologous to the single-stranded nucleic acid and mediate formation of the triplex structure in the region.

In the term "RecA protein" are therefore included the RecA-like protein as well as RecA proteins derived from *E. Coli* and lambda phage. As described above, in the present method, the RecA-like protein can be used so long as it has a function that promotes coupling of homologous DNAs and catalyze the formation of a triplexed DNA.

Preferable RecA protein used for the invention is that derived from *E. Coli*.

The term "DNA library" means a group of various DNA fragments and is generally used herein as a general term referring both to a gene library and a cDNA library. The "gene library" means a panel of whole DNA fragments in a single species contained in phages or cosmids, and is equivalent to a "Genomic DNA library". The "cDNA library" means a panel of various cDNA species produced by inserting, into vectors, complementary DNAs (hereinafter referred to as cDNAs) prepared from mRNAs derived from a given tissue or a cell. The DNA fragments may not be circularized by being incorporated into phages, cosmids, or plasmids, thus the library may consist only of the DNA fragments. The DNA library may contain any kinds, for example two kinds of the DNA fragments.

Double-stranded DNA and single-stranded DNA are abbreviated herein to dsDNA and ssDNA, respectively.

Now, we describe the method of the invention in more detail.

In the first embodiment of the invention, there is provided a method of constructing a circular DNA library having increased proportion of a desired nucleic acid by removing a given DNA from an original circular DNA library using RecA protein. In the first step of the method according to the invention, a circular DNA in the original library are converted into a linearized DNA. To convert a circular DNA into a linearized DNA, for example, the circular DNA may be cleaved with a proper restriction enzyme. Preferably, the restriction enzyme cleaves the circular DNA at only one site. General procedures can be used for cleavage with the restriction enzyme. Then in the second step, an ssDNA is prepared corresponding to a second dsDNA to be removed from the DNA library.

As used herein, the term "corresponding to" a second dsDNA to be removed means that the ssDNA comprises, in either strand, a portion having a nucleotide sequence substantially same with whole or part of the second dsDNA. The term "having a nucleotide sequence substantially same" means that a given DNA has a nucleotide sequence equivalent enough for allowing a formation of a triplexed DNA by RecA protein.

The second dsDNA may be 3–13 kb in size. Preferably, it is 6 kb or more and is contained in a size-fractioned library.

These dsDNAs in the library are usually carried on plasmids or virus vectors.

For the preparation of an ssDNA corresponding to the second dsDNA, an in vitro transcription system may be used. SP6 Transcription System (Ambion co.) is applied to inserts in a DNA library transferred onto pSPORT1, an in vitro transcription vector, to synthesize RNA. Then, cDNA is synthesized with appropriate primes such as Rondom primer N6 (Takara Syuzo co., Ltd.) and reverse transcriptase such as SuperScript II RT (Invitrogen co.). Finally, purification of cDNA by removal of proteins with phenol/chloroform will give ssDNA. A method for cDNA preparation described above is well known to those skilled in the art.

In order to generate ssDNA corresponding to a dsDNA in a library, dsDNA also may be treated with nuclease such as ExoIII and T7 gene 6 following introduction of a nick into the dsDNA with nickase and the like. Procedures for converting dsDNA into ssDNA include, but not limited to, recovering the ssDNA with phagemid vectors like pBluescript, pGEM, and pUC119 as phage particles.

Subsequently, in the third step, the RecA protein and the second ssDNA are added to the DNA library.

As described above, the ssDNA corresponding to the second dsDNA generated contains in either strand a nucleotide sequence identical to whole or part of the second dsDNA. Accordingly, addition of the second ssDNA prepared in the previous step and RecA protein to the second dsDNA will cause a progress of triplexed DNA forming reaction (see FIG. 2).

For the length of the ssDNA, at least 10 or more, preferably 15 or more, preferably 20 or more, more preferably 30 or more, even more preferably 40 or more, most preferably 60 base pair long or more is desirable to keep the triplex structure stable after dissociation of the RecA protein from the structure.

For stable formation of the triplex structure, an outer (i.e. terminal-end side of the dsDNA) one of both terminals in the triplex structure is preferably located outside the fiftieth, more preferably thirtieth, more preferably twentieth, and even more preferably tenth base from the terminal end of the dsDNA.

The presence of ATP in a sample will cause progress of homologous recombination and instant breakdown of generated triplex structure, because the RecA protein normally catalyzes homologous recombination in the presence of ATP.

Addition of an alternative to ATP such as GTP and ITP or a non-degradable analogue of ATP such as ATP γ S is required for the formation of triplex structure by RecA protein. It is known that exchange reaction mediated by RecA protein does not proceed in the presence of GTP or ITP.

Then, in the fourth step, self-ligation reaction is performed on DNAs containing the triplexed DNA generated in the previous step. Whereas self-ligation dose not occur on a DNA in which the triplex structure has been formed, it occurs on a dsDNA in which the triplex structure is not formed, giving a circular DNA.

As used herein, the term "self-ligation" means the formation of circular DNA by ligation of 5' and 3' terimanls of a given linear DNA.

The ligation reaction may be performed with general methods. A ligation reaction (37° C., 30 min) by T4 DNA Ligase (Invitrogen co.) can construct a circular DNA. Other commercially available ligation kits can also be used.

In the invention, a cycle of the first to fourth steps above can be repeated more than once.

In the fifth step, linear DNAs are removed from DNAs prepared in the previous step to construct a DNA library having increased proportion of the first dsDNA.

In order to separate a linear triplexed DNA and a circular DNA to be increased in proportion, separation with agarose gel electrophoresis and centrifugation in the presence of ethidium bromide can be used. If a DNA library used contains a drug resistance gene, the DNA may be, but not limited to, transformed into hosts to select a host transformed with a circular DNA using a drug.

In the present method, a triplex formation step by the RecA protein can be followed by a step for dissociating RecA protein from the triplex.

Figure 2:
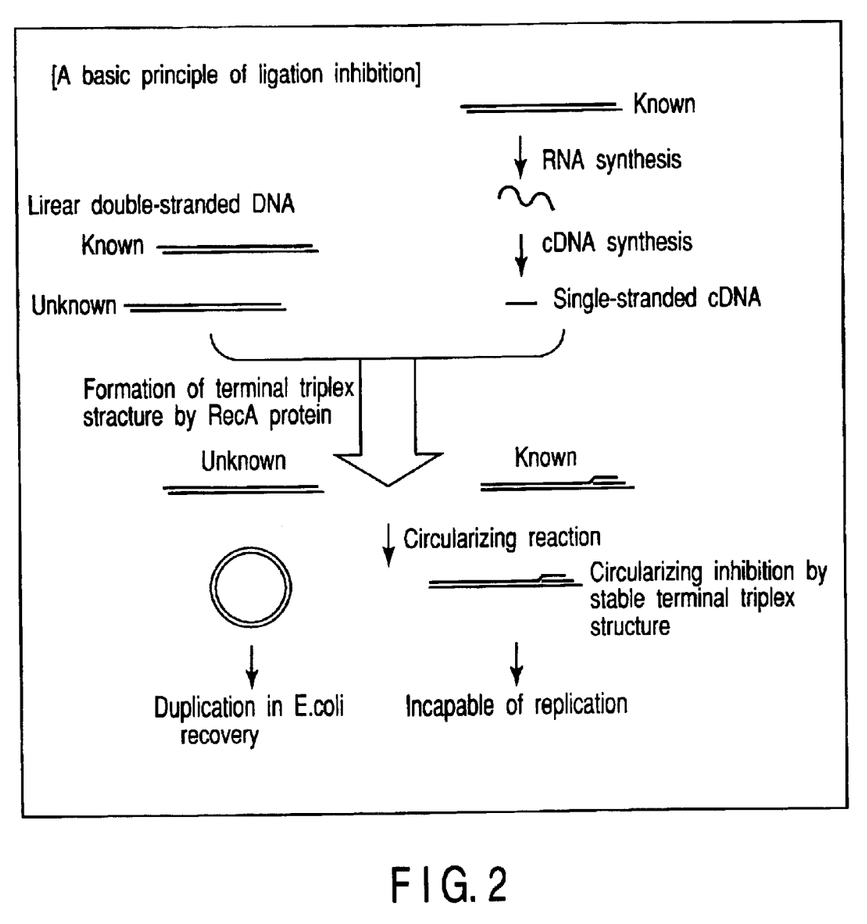
FIG. 2 illustrates a basic principle of ligation inhibition in the invention.
Figure 3:
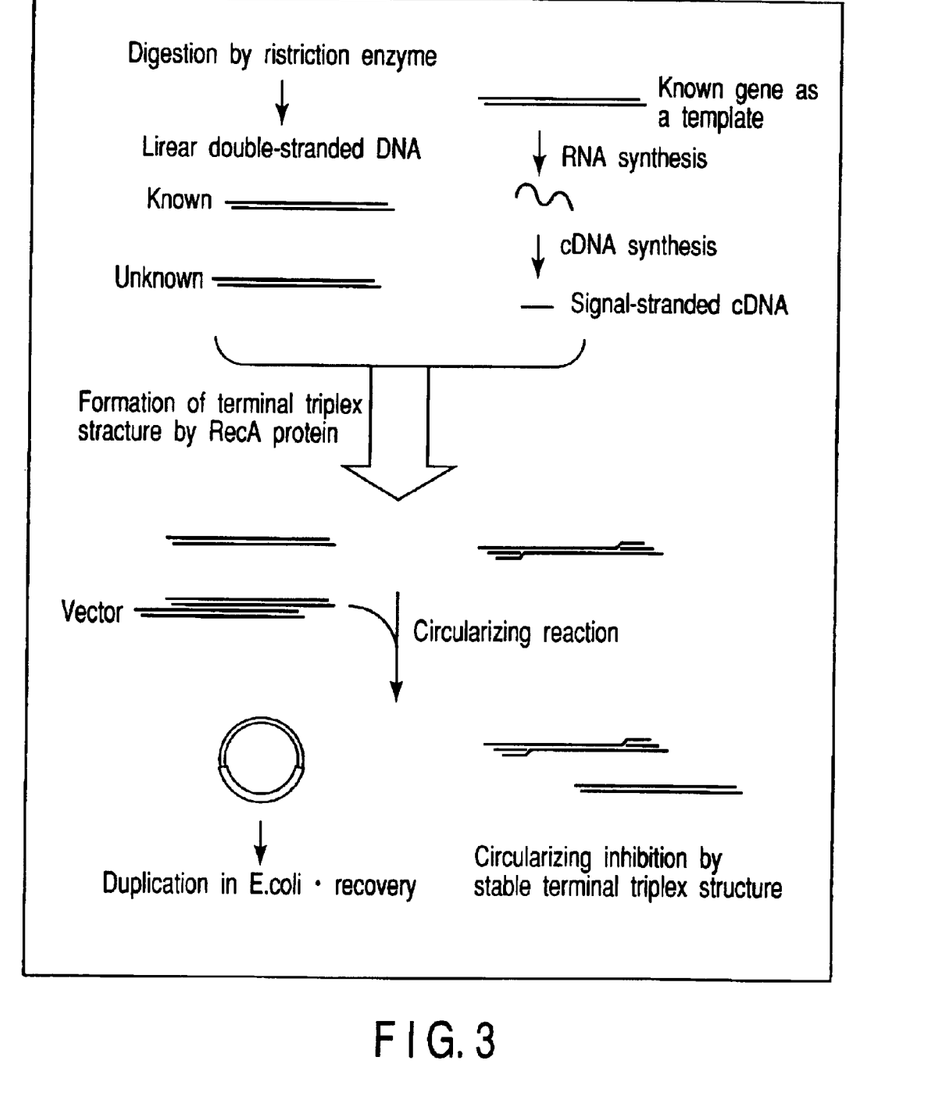
FIG. 3 illustrates a basic principle of ligation inhibition in the invention.

For convenience, one out of two dsDNAs is removed in FIG. 2 and the description above. However, note, according to the method, that dozens to tens of thousands of dsDNAs can simultaneously or sequentially be removed from thousands to tens of thousands of dsDNAs.

In the second embodiment of the invention, a method is provided to construct a DNA library having increased proportion of a desired nucleic acid by removing a specific DNA from a DNA library with better efficiency than using the method according to the first embodiment. More specifically, a method is provided in which efficiency of ligation inhibition by RecA protein is improved by inhibiting ligation reaction on both terminals in a nucleic acid.

In the first step of the method, a linear DNA library is prepared. Linear DNA can be prepared by cleaving off a DNA fragment from circular DNA or by PCR method. Generation of cDNA by reverse transcription of mRNA can also be used for the preparation of linear DNA. Various other methods can be used to obtain a DNA fragment. For the case of cDNA libraries, for example, it can be prepared by cleaving off insert cDNA inserted in a vector.

General procedures can be utilized for cleavage of the DNA, PCR, reverse transcription from mRNA, and other preparation for linear DNA.

Subsequently, in the second step, ssDNAs are prepared corresponding to both terminal sequence in the dsDNA removed from the DNA library. As used herein, "both terminal sequence" refers to the 5' and the 3' terminal sequence in the second dsDNA.

As used herein, "corresponding to both terminal sequences" means that each ssDNA includes, in any region, 5' terminal or 3' terminal sequence in the second dsDNA or a nucleotide sequence substantially identical to portions thereof. The term "having a nucleotide sequence substantially identical" means, as described above, having the sequence equivalent enough for allowing the formation of triplexed DNA by RecA protein.

Then, in the third step, the RecA protein and the second ssDNA are added to the DNA library. As described above, this step causes the progress of triplexed DNA formation reaction.

Next in the fourth step, DNAs containing the triplexed DNA obtained in the previous step are ligated with a desired DNA. While ligation does not occur on triplexed DNA, ligation occurs on untriplexed dsDNA, giving circular DNA.

In this method, "a desired DNA" generally, although not necessarily, means a vector for constructing a library like phages, cosmids, and plasmids.

In the fifth step, removal of linear DNA from the DNAs prepared in the previous step constructs a DNA library having increased proportion of the first dsDNA.

Linear triplexed DNA to be removed can be separated from circular DNA to be increased in proportion as described above.

Specific reactions and structures illustrated in the drawings are intended merely to help understanding. Accordingly, their details may not be consistent with those shown in figures.

The invention is further illustrated in more detail by the following examples.

EXAMPLES

Example 1

In this example, we removed one plasmid from a mixture of two plasmids by ligation inhibition reaction using RecA protein. We used a chloramphenicol-resistant plasmid pBC23C10 and an ampicillin-resistant plasmid pBS1B3, and removed one plasmid from the mixture of the two plasmids. pBC23C10 and pBS1B3 were mixed at the ratio of 1000:1, and digested at one site with restriction enzyme NotI to give linear dsDNA. Following cleavage of pBC23C10 with SalI and NotI, pSPORT1 (Invitrogen co.) cleaved with SalI and NotI in advance and insert DNA were ligated. After transferring onto pSPORT1 competent for in vitro transcription, we synthesized RNA using SP6 Transcription System (Ambion Inc.). 6.25 $\mu$g of Random primer N6 (Takara Shuzo co., Ltd.) was added to 5 $\mu$g of the resulting RNA, heat denatured, and rapidly cooled with iced water. 40 units of RNase inhibitor (Toyobo co., Ltd.), 4 $\mu$l of 5×First strand Buffer (Invitrogen co.), 2 $\mu$l of 0.1M dithiothreitol, and 1 $\mu$l of 10 mM dNTP Mix (Invitrogen co.) were added. After addition of 5 $\mu$l of SuperScript II RT (Invitrogen co.), sterilized distilled water was added to 20 $\mu$l. cDNA was synthesized by a reaction at 37° C. for 60 minutes. The cDNA was purified by removal of protein with phenol/chloroform. Triplex-forming reaction mixture I contained, in a total volume of 20 $\mu$l, added 30 mM Tris-acetate (pH 6.9), 1 mM magnesium acetate, 1 mM dithiothreitol, 100 ng of synthesized pBC23C10-derived cDNA, 5 $\mu$g of RecA protein (EPICENTRE co.) and sterilized distilled water, and was warmed at 37° C. for 15 minutes. Triplex forming reaction mixture II contained, in a total volume of 18 $\mu$l, 30 mM Tris-acetate (pH 6.9), 23 mM magnesium acetate, 1 mM dithiothreitol, 50 ng of NotI-cleaved library and sterilized distilled water. It was mixed with the triplex-forming reaction I and warmed at 37° C. for 30 minutes. After addition of 2 $\mu$l of 100 mM GTP, reaction at 37° C. for 30 minutes was carried out. Following a proteolysis procedure, DNA is purified. Ligation reaction was performed for 30 minutes at 37° C. with T4 DNA Ligase (Invitrogen co.). Then DNA was purified and a library was reconstructed by transforming E. Coli with the purified DNA. It is revealed that only a plasmid to be removed has been selectively decreased to 1/400.

TABLE 1

Selective removal of one plasmid from a mixture of two plasmids

| | E. Coli colony number | |
|---|---|---|
| | Before removal | After removal |
| Chloramphenicol resistant | 4690000 | 11300 |
| Ampicillin resistant | 30100 | 37300 |

Example 2

We removed previously cloned plasmids (3000 clones) from a plasmid library by triplex formation reaction using RecA protein. Plasmid library inserts constructed in pBlueScript SKII (+) were transferred onto pSPORT1 (Invitrogen co.), an in vitro transcription vector, to synthesize RNA with SP6 transcription System (Ambion, Inc.). 6.25 $\mu$g of Random primer N6 (Takara Shuzo co., Ltd.) was added to 5 $\mu$g of the resulting RNA, heat-denatured, and rapidly cooled with iced water. 40 units of RNase inhibitor (Toyobo co., Ltd.), 4 $\mu$l of 5×First strand Buffer (Invitrogen co.), 2 $\mu$l of 0.1M dithiothreitol, and 1 $\mu$l of 10 mM dNTP Mix (Invitrogen co.) were added. After addition of 5 $\mu$l of SuperScript II RT (Invitrogen co.), sterilized distilled water was added to 20 $\mu$l. cDNA was synthesized by a reaction at 37° C. for 60 minutes. Removal of proteins with phenol/chloroform provided purified cDNA. The plasmid library was digested into linear dsDNA with a restriction enzyme NotI that cleaves plasmid DNA at only one site. Triplex-forming reaction mixture I contained, in a total volume of 20 $\mu$l, 30 mM Tris-acetate (pH 6.9), 1 mM magnesium acetate, 1 mM dithiothreitol, 100 ng of synthesized cDNA, 5 $\mu$g of RecA protein (EPICENTRE co.) and sterilized distilled water, and was warmed at 37° C. for 15 minutes. Triplex-forming reaction mixture II contained, in a total volume of 18 $\mu$l, 30 mM Tris-acetate (pH 6.9), 23 mM magnesium acetate, 1 mM dithiothreitol, 50 ng of NotI-cleaved library and sterilized distilled water, was mixed with the triplex-forming reaction mixture I, and then was warmed at 37° C. for 30 minutes. After addition of 2 $\mu$l of 100 mM GTP, reaction at 37° C. for 30 minutes was carried out. Following a proteolysis procedure, DNA was purified. Ligation reaction was performed for 30 minutes at 37° C. with T4 DNA Ligase (Invitrogen co.). Then DNA was purified and the library was reconstructed by transforming E. Coli with the purified DNA. We sequenced randomly selected 96 clones, and evaluated the frequency of occurrence of unknown clones by comparing their sequences to those of known clones in a database. A single round of procedure for removing known clones raised the frequency from about 60% to about 80%.

TABLE 2

Occurrence of a novel clone after removal

| Library | Occurrence of a novel clone |
|---|---|
| Before removal | 58.3% |
| After removal | 77.0% |

Example 3

For the purpose of improving efficiency of the ligation inhibition reaction using RecA protein, we removed one plasmid from a mixture of two plasmids by inhibiting the ligation of both terminals of a gene.

The plasmids were digested with restriction enzymes NotI and MulI that cleave both ends of inserted genes. T7 Transcription System (Ambion co.) and T3 (Ambion co.) Transcription System were used to synthesize RNA with the digested plasmids as templates. 6.25 µg of Random primer N6 (Takara Shuzo co., Ltd.) was added to 5 µg of the resulting RNA, heat denatured, and rapidly cooled with iced water. 40 units of RNase inhibitor (Toyobo co., Ltd.), 4 µl of 5× First strand Buffer (Invitrogen co.), 2 µl of 0.1M dithiothreitol, and 1 µl of 10 mM dNTP Mix (Invitrogen co.) were added. After addition of 5 µl of SuperScript II RT (Invitrogen co.), sterilized distilled water was added to 20 µl. cDNA was synthesized by a reaction at 37° C. for 60 minutes. Removal of proteins with phenol/chloroform provided purified cDNA. To excise the inserted genes, the plasmids were digested with NotI and MulI, a combination of restriction enzymes that cleave both ends of inserted genes. Triplex-forming reaction mixture I contained, in a total volume of 20 µl, 30 mM Tris-acetate (pH 6.9), 1 mM magnesium acetate, 1 mM dithiothreitol, 100 ng each of synthesized cDNAs corresponding to each end, 5 µg of RecA protein (EPICENTRE inc.) and sterilized distilled water, and was warmed at 37° C. for 15 minutes. Triplex forming reaction mixture II contained, in a total volume of 18 µl, 30 mM Tris-acetate (pH 6.9), 23 mM magnesium acetate, 1 mM dithiothreitol, 50 ng of NotI- and MulI-cleaved plasmids and sterilized distilled water, and was warmed at 37° C. for 30 minutes. It was mixed with the triplex-forming reaction I and warmed at 37° C. for 30 minutes. After addition of 2 µl of 100 mM GTP, reaction at 37° C. for 30 minutes was carried out. Following proteolysis procedure, DNA was purified. Ligation reaction was performed for 30 minutes at 37° C. with T4 DNA Ligase (Invitrogen co.). We then purified DNA, and transformed *E. Coli* with the purified DNA to evaluate effects on ligation inhibition.

Addition of cDNAs each corresponding to each end of the inserted genes showed synergistic inhibitory effect, when compared to addition of only one cDNA.

TABLE 3

Result of selective removal of clone using ligation inhibition by formation of triplex structure in both end

| Gene clone | No formation of triplex | Formation of triplex in the 5' terminal | Formation of triplex in the 3' terminal | Formation of triplex in both end |
|---|---|---|---|---|
| 23C10 | 4960000 | 120000 (1/41) | 29100 (1/170) | 860 (1/5767) |
| 39E01 | 5390000 | 37400 (1/144) | 42400 (1/127) | 373 (1/14450) |

The figures in the Table 3 illustrate colony numbers. In the parentheses of the lower panel, ratios of colony numbers obtained with ligation inhibition reaction to those obtained without the reaction are illustrated.

The method of the present invention enables a direct construction of a DNA library having increased proportion of a desired nucleic acid by removing nucleic acids other than the desired acid from an original DNA library. As demonstrated in the above examples, 90% or more known dsDNA can be removed by the method of the invention.

Moreover, a method wherein the triplex structure is introduced in both ends of dsDNA can lower the amount of known genes to one-hundredth, in contrast to a method which introduces the structure in either end. Depending on types of library to which the invention is applied, frequency of occurrence of a novel clone in the library will increase by 10–99%.

What is claimed is:

1. A method of constructing a circular DNA library having increased proportion of a first double-stranded DNA by removing from an original circular DNA library, a second double-stranded DNA that is not identical to the first double-stranded DNA, said method comprising the following steps:
   (1) linearizing circular DNA in an original circular DNA library comprising a first double-stranded DNA and a second double-stranded DNA to form a linear DNA library;
   (2) preparing single-stranded DNA corresponding to the second double-stranded DNA;
   (3) adding RecA protein and the single-stranded DNA to the linear DNA library to produce a mixture, wherein the mixture comprises linear first double-stranded DNA and triplexed DNA, and wherein the triplexed DNA is formed through the binding of the second double-stranded DNA and the single-stranded DNA prepared in step (2) via the RecA protein;
   (4) subjecting the mixture formed in step (3) to self-ligation to selectively circularize double-stranded DNA that dose not contain a triplex; and
   (5) removing noncircular DNA from the ligated mixture formed in step (4) to produce a circular DNA library having increased proportion of the first double-stranded DNA in comparison to the original DNA library.

2. The method of claim 1, wherein in step (5) the noncircular DNA is removed from the circularized DNA formed in step (4) by transforming a host with the circularized DNA in step (4) using drug selection.

3. A method of constructing a circular DNA library having increased proportion of a first double-stranded DNA by removing from an original circular DNA library, a second double-stranded DNA that is not identical to the first double-stranded DNA, said method comprising the following steps:
   (1) linearizing circular DNA in an original circular DNA library comprising a first double-stranded DNA and a second double-stranded DNA to form a linear DNA library;
   (2) preparing a single-stranded DNA mixture comprising a first single-stranded DNA corresponding to the 5' end of the second double-stranded DNA and a second single-stranded DNA corresponding to the 3' end of the second double-stranded DNA;
   (3) adding RecA protein and the single-stranded DNA mixture to the linear DNA library to produce a second mixture, wherein the second mixture comprises linear first double-stranded DNA and triplexed DNA, and wherein the triplexed DNA is formed through the binding of the second double-stranded DNA and the single-stranded DNA mixture prepared in step (2) via the RecA protein;
   (4) subjecting the second mixture formed in step (3) to ligation with a desired DNA under conditions to selectively circularize double-stranded DNA that does not contain a triplex; and
   (5) removing noncircular DNA from the ligated second mixture formed in step (4) to produce a circular DNA library having increased proportion of the first double-stranded DNA in comparison to the original DNA library.

4. The method of claim 3, wherein in step (5) the noncircular DNA is removed from the circularized DNA formed in step (4) by transforming a host with the circularized DNA in step (4) using drug selection.

* * * * *

UNITED STATES PATENT AND TRADEMARK OFFICE
CERTIFICATE OF CORRECTION

PATENT NO. : 6,867,001 B2
DATED : March 15, 2005
INVENTOR(S) : K. Kondo et al.

It is certified that error appears in the above-identified patent and that said Letters Patent is hereby corrected as shown below:

Column 10,
Line 24, "dose" should read -- does --

Signed and Sealed this

Twenty-eighth Day of June, 2005

JON W. DUDAS
*Director of the United States Patent and Trademark Office*